United States Patent [19]

Boarman

[11] Patent Number: 4,834,114
[45] Date of Patent: May 30, 1989

[54] CONTRACEPTIVE SYSTEM

[76] Inventor: George L. Boarman, 13187 Highland Rd., Highland, Md. 20777

[21] Appl. No.: 51,324

[22] Filed: May 19, 1987

[51] Int. Cl.⁴ .............................................. A61F 5/42
[52] U.S. Cl. ................... 128/830; 128/844; 604/347
[58] Field of Search .............. 604/346, 347, 349, 351, 604/353; 128/79, 132 R, 138 R

[56] References Cited

U.S. PATENT DOCUMENTS

| | | | |
|---|---|---|---|
| 87,932 | 3/1969 | Hoffman | 604/349 |
| D. 288,485 | 2/1987 | Denno | D24/51 |
| 2,406,600 | 8/1946 | Forestiere | 128/132 R |
| 2,445,220 | 7/1948 | Isaacson | 604/349 |
| 2,525,238 | 10/1950 | Penska | 604/349 |
| 2,591,783 | 4/1952 | Craddock | 604/353 X |
| 2,816,542 | 12/1957 | Freeman | 128/844 |
| 3,536,066 | 10/1970 | Ludwig | 604/347 X |
| 3,759,254 | 9/1973 | Clark | 604/349 X |
| 4,004,591 | 1/1977 | Freimark | 128/132 R X |
| 4,036,220 | 7/1977 | Bellasalma | 128/132 R |
| 4,553,968 | 11/1985 | Komis | 604/349 |
| 4,588,397 | 5/1986 | Giacalone | 604/351 X |
| 4,664,104 | 5/1987 | Jaicks | 604/353 X |
| 4,735,621 | 4/1988 | Hessel | 604/351 X |

FOREIGN PATENT DOCUMENTS

| | | | |
|---|---|---|---|
| 0119143 | 9/1984 | European Pat. Off. | 604/349 |
| 0254211 | 11/1912 | Fed. Rep. of Germany | 604/349 |
| 0366492 | 10/1906 | France | 604/349 |
| 117234 | 10/1926 | Switzerland | 604/349 |
| 0264690 | 1/1927 | United Kingdom | 604/349 |

Primary Examiner—Dalton L. Truluck
Attorney, Agent, or Firm—Morton J. Rosenberg

[57] ABSTRACT

A contraceptive system (10) is provided for use by both men and women having one piece formation which includes an extended tubular member (12) coupled to a genital shield member (14). Extended tubular member (12) is closed at the distal end (30) and open at the proximal end (32). In the embodiment adapted for use by women, extended tubular member (12) has a non-uniform wall thickness where the bottom wall thickness (36) is greater than the top wall thickness (34). Genital shield (14) includes an absorbent layer (16) adhesively bonded to the surface (15) of shield member (14). Shield member (14) also includes retention straps (18) with clasps (20) for maintaining contraceptive system (10) in position on the body.

17 Claims, 2 Drawing Sheets

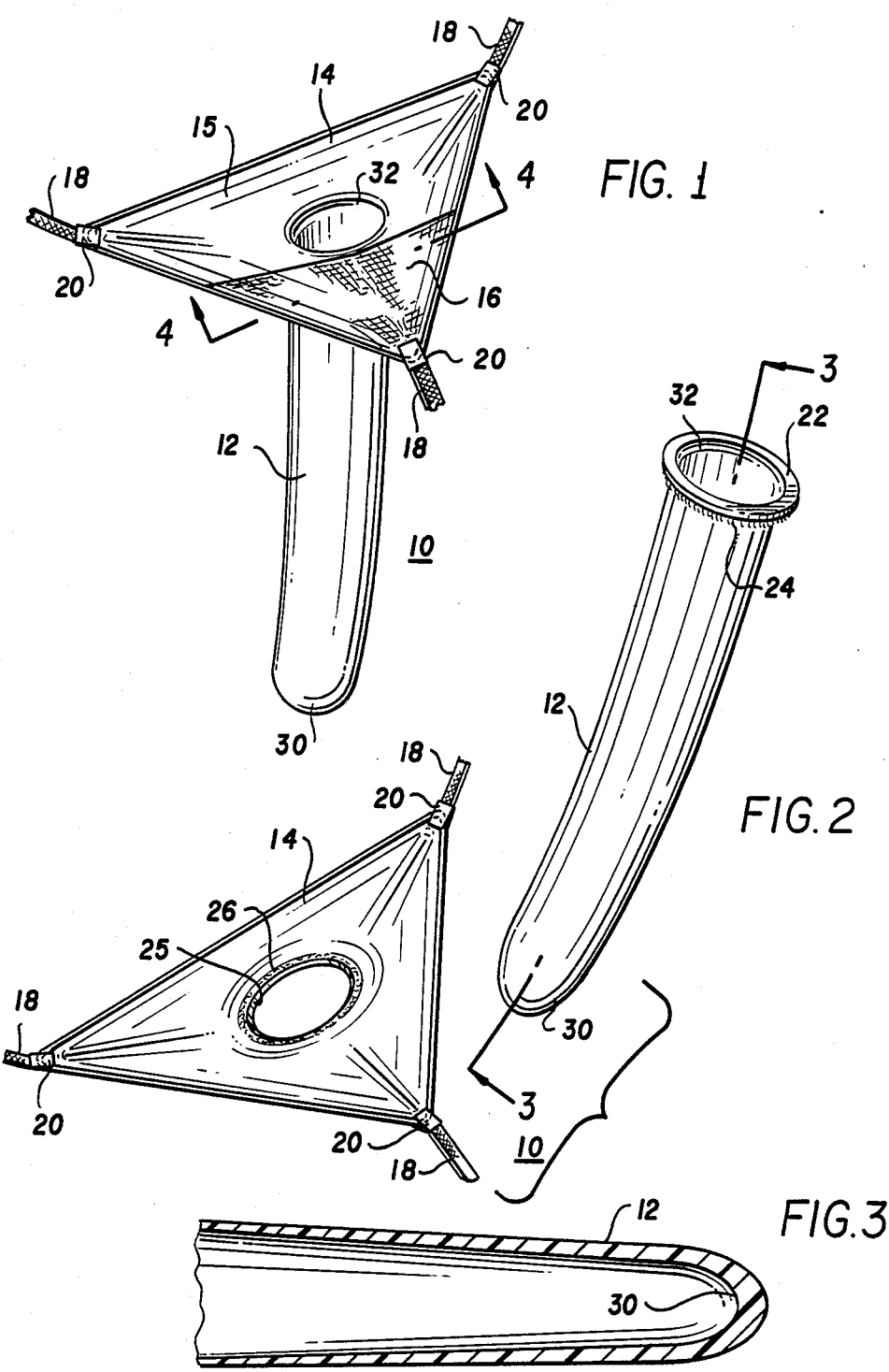

CONTRACEPTIVE SYSTEM

BACKGROUND OF THE INVENTION

1. Field of the Invention

This invention directs itself to contraceptive systems. In particular, this invention directs itself to contraceptive systems having an extended tubular member for insertion into the vaginal cavity. More in particular, this invention directs itself to contraceptive systems having an extended tubular member secured to a shield-like member. Still further, this invention relates to a contraceptive system which incorporates retention straps for releasably coupling the shield like member to the individual using the contraceptive system. Still further, this invention relates to a contraceptive system wherein the extended tubular member has a non-uniform wall thickness where the bottom wall thickness is greater than the upper wall thickness. Still further, this invention pertains to a contraceptive system formed of a rubber-like composition in one-piece formation. Still further, this invention pertains to a contraceptive system where the shield-like member includes a layer of absorbent material adhesively bonded to the outside surface of the shield-like member.

2. Prior Art

Contraceptive systems having an extended tubular member are well-known in the art. However, contraceptive systems having an extended tubular member having a non-uniform wall thickness secured to a shield mechanism all of a one-piece formation has not been found in the prior art.

The best prior art known to the Applicant are U.S. Pat. Nos. 2,591,783; 4,568,340; 4,553,968; 3,032,038; 4,232,675; 3,999,550; 1,866,060; 713,900; 2,389,831; 3,677,225; and, 4,354,494.

In some prior art references, such as shown in U.S. Pat. No. 2,591,783, there are provided a protecting shield having a centrally located opening for insert of a tubular protecting member. Such prior art systems do not provide for a tubular member and protecting shield formed in one-piece formation with an absorbent material bonded to one surface of the shield member. Nor do they provide for a tubular member having a non-uniform wall thickness as does the subject inventive concept.

Other prior art systems direct themselves to various devices having tubular members coupled to retention or support straps, but lack the shield member secured to the tubular member as provided in the subject inventive concept.

SUMMARY OF THE INVENTION

A contraceptive system which includes a prophylactic mechanism for insertion into the vaginal cavity. The prophylactic mechanism includes an extended tubular member having a non-uniform wall thickness, whose distal end is closed, and whose proximal end is open. A shield mechanism which covers the lower abdominal area of the individual using the system is secured to the open proximal end of the extended tubular member. A releasable fastener mechanism secures the shield mechanism to the individual using the contraceptive system.

BRIEF DESCRIPTION OF THE DRAWINGS

FIG. 1 is a perspective view of the system;

FIG. 2 is a perspective view of another embodiment of the system;

FIG. 3 is a partial sectional view of the embodiment of the system taken along the Section Line 3—3 of FIG. 2;

DESCRIPTION OF THE PREFERRED EMBODIMENTS

Figure 4:
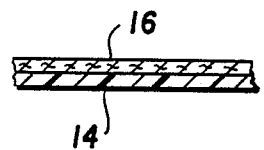
FIG. 4 is a sectional view of the embodiment of the system taken along Section Line 4—4 of FIG. 1; and, FIG. 5 is a partial sectional view of another embodiment of the system taken along the Section Line 3—3 of FIG. 2.

Referring to FIGS. 1 and 2, there is shown system 10 for contraception and prophylaxis enhancement. Contraceptive system 10 is adaptable for use by both men and women as a contraceptive, as well as a means to aid in the prevention of communicable disease transmission through intimate sexual contact.

In overall concept, contraceptive system 10 provides a condom like element 12 coupled to a genital shield which enhances the prophylactic properties of the condom like element 12. Contraceptive system 10 provides a contraceptive method to women which has been proven safe and effective, but has up to now not been available for their use. While the condom is considered the best means for preventing the transmission of venereal type diseases and simultaneously preventing conception, it is heretofore only been available for use by men. Contraceptive system 10 however, enhances and improves on the prior art condom by providing a genital shield to further preclude a chance of disease transmittal through intimate sexual contact. Genital shield 14 further includes an absorbent material layer 16 to further enhance the disease prevention qualities of contraceptive system 10.

Referring now to FIG. 1, there is shown contraceptive system 10 for use by women as a means of contraception and prophylaxis. Contraceptive system 10 includes an extended tubular member 12 having a closed distal end 30 for insertion into the vaginal cavity of the female using contraceptive system 10. Tubular member 12 has an open proximal end 32 to permit insertion of the penis of a male sexual partner while maintaining a barrier between the penis and the vaginal cavity walls.

As an improvement over prior art condom devices, contraceptive system 10 includes genital shield 14 coupled to the proximal end 32 of tubular member 12. Genital shield 14 is a cuneiform, or wedge-shaped member formed at the proximal end of tubular member 12. Tubular member 12 and genital shield 14 are formed of a latex rubber material molded in a one-piece formation by methods well-known in the art. To further enhance the prophylactic characteristics of contraceptive system 10, an absorbent material 16 is bonded to the outside surface 15 of genital shield 14. The composition of absorbent material 16, although not important to the inventive concept, may be any one of a number of cloth or paper compositions having high absorbency.

Thus, contraceptive system 10 is provided for use by a female having tubular member 12 with closed distal end 30 for insertion into the vaginal cavity. Tubular member 12 includes a genital shield 14 formed at the open proximal end 32 of tubular member 12. Genital shield 14 further includes absorbent layer 16 adhesively bonded to surface 15 of genital shield 14.

Of particular importance to the inventive concept of contraceptive system 10 is the means for retention of tubular member 12 within the vaginal cavity. Referring now to FIG. 3, there is shown a cut-away sectional view of tubular member 12 which clearly shows the non-uniform wall thickness of tubular member 12, which increases substantially at the distal end 30. The non-uniform wall thickness of tubular member 12 increases gradually from the open proximal end 32 to the closed distal end 30, as is shown in the Figure. The increased wall thickness at the distal end 30 of tubular member 12 functions to stiffen the distal end 30, and thus provides a means for retention within the vaginal cavity.

Figure 5:
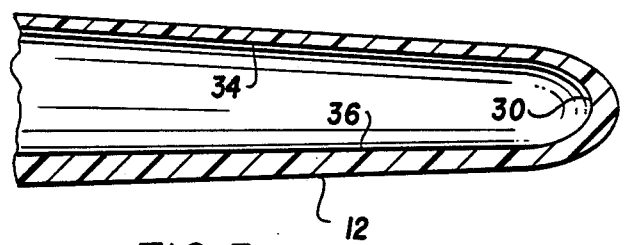

Referring now to FIG. 5, there is shown a cut-away sectional view of an alternate embodiment of tubular member 12. As shown in the Figure, the non-uniform wall thickness is distributed such that the bottom surface 36 and the closed distal end 30 have substantially increased wall thickness when compared with top surface 34 of tube member 12. The increased wall thickness of bottom surface 36 increases the rigidity of that portion of tubular member 12 and therefore provides a means for retention of tubular member 12 within the vaginal cavity.

Contraceptive system 10 provides a unique system for implementing a condom like contraceptive for use by women. As shown in FIGS. 1, 3 and 5, the non-uniform wall thickness of tubular member 12 uniquely provides a means for retention of tubular member 12 within the vaginal cavity. The increased wall thickness, as previously stated, increases the rigidity of tubular member 12 in the longitudinal direction to maintain tubular member 12 position within the vaginal cavity.

The operable location of contraceptive system 10 is further maintained with the aid of retention straps 18 coupled to the vertices of genital shield 14. Retention straps 18 are fastened around the body of a user to assist in maintaining the location of genital shield 14 in proper contact with the lower abdominal area of the user. Thus, three retention straps 18 are provided, coupled at one end to shield member 14 and tied or clasped together at the opposing ends. Hence, two straps pass around the waist of the user, while the third passes between the legs to be joined with the two fastened around the waist. Retention straps 18 may be permanently bonded to shield member 14 with adhesives or similar techniques. As an alternative, retention straps 18 may be releasably coupled to shield member 14 by clasp 20, allowing retention straps 18 to be reusable. Clasp 20 may be a small spring loaded clamping device well-known in the apparel art.

Referring now to FIG. 2, there is shown an alternate embodiment for contraceptive system 10 where extended tube member 12 is releasably coupled to genital shield 14 for use by either a male or female. As shown, genital shield 14 has a hole 25 formed therethrough for insertion of extended tube member 12 prior to use of contraceptive system 10. Surrounding hole 25 in shield member 14 is an annular ring of Velcro material 26 for releasable coupling with extended tube member 12.

When the embodiment of contraceptive system 10 shown in FIG. 2 is intended for use by a female, the extended tube member 12 will have the non-uniform wall thickness construction as previously described. In addition, extended tubular member 12 has an annular attachment flange 22 located at the open proximal end 32. The underside of annular flange 22 is adhesively bonded to an annular ring of Velcro material 24, providing a releasable Velcro coupling between extended tube member 12 and genital shield 14.

As an alternate embodiment, attachment flange 26 surrounding hole 25 of genital shield 14, may be coated with an adhesive for fixedly coupling a commercial condom to genital shield 14. This alternative permits a male to apply a commercially available condom to contraceptive system 10. In this embodiment, the male would first apply the condom to his penis, and then insert the sheathed penis through hole 25 of genital shield 14 such that the adhesive coated flange is brought into contact with the rolled flange of the commercial condom. Subsequently, the male user would couple retention straps 18 around his waist and between his legs, as has been previously described.

The alternate embodiment shown in FIG. 2 has been shown to provide a releasably coupled contraceptive system employing the inventive concept herein described. Genital shield member 14 has a hole 25 formed therethrough, with attachment flange 26 for releasably coupling extended tubular member 12 to genital shield 14. Tubular member 12 similarly has annular flange 22 formed at the proximal end 32 for matingly coupling with attachment flange 26. Attachment flange 26 and annular flange 22 may each be coupled to one part of a Velcro attachment system for providing the releasable coupling between tubular member 12 and genital shield 14. As an alternative, attachment flange 26 may be coated with an adhesive for fixedly coupling annular flange 22 of tubular member 12 or the rolled flange of a commercially available condom. When the embodiment shown in FIG. 2 is to be used by a female, tubular member 12 incorporates the inventive concept of a non-uniform wall thickness for increasing the rigidity of tubular member 12, thus aiding in the retention of tubular member 12 within the vaginal cavity.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed all without departing from the spirit or scope of the invention as defined in the appended claims.

What is claimed is:

1. A system for contraception and prophylaxis enhancement for use by females, comprising:
    (a) prophylactic means for at least partial insertion into the vaginal cavity of a dimension sufficient to substantially interface with a wall of said vaginal cavity including an extended tubular member, said tubular member defining a closed distal end and an open proximal end having a bottom surface extending therebetween, said tubular member having a non-uniform wall thickness wherein said bottom surface of said tubular member defines an area of increased wall thickness, said non-uniform wall thickness extending substantially throughout an extended length of said tubular member for increasing he rigidity thereof, said area of increased wall thickness defining a means for retaining said prophylactic means within said vaginal cavity;

(b) shield means positionally located contiguous a lower abdominal area of said user being secured to said prophylactic means; and, (c) means for releasably coupling said shield means to said user.

2. The system as recited in claim 1 where said shield means defines a cuneiform shaped protective cover for said lower abdominal area.

3. The system as recited in claim 2 where said shield means and said prophylactic means are formed in a one-piece formation.

4. The system as recited in claim 1 where said means for releasably coupling said shield means to said individual includes a plurality of attachment strap members coupled to said shield means.

5. The system as recited in claim 4 where said plurality of attachment strap members are releasably coupled to said shield means on a first end.

6. The system as recited in claim 5 where each of said attachment strap members are adapted on a second end for coupling one to the other.

7. The system as recited in claim 3 where said cuneiform protective cover includes an outer layer of absorbent material formed thereon.

8. The system as recited in claim 2 where said cuneiform shaped protective cover is adapted for releasable coupling to said tubular member.

9. The system as recited in claim 8 where said protective cover having a hole formed therethrough for insert of said tubular member.

10. The system as recited in claim 9 where said tubular member is a condom, said condom having an annular flange at said proximal end.

11. The system as recited in claim 10 where said hole formed through said protective cover is bounded by an attachment flange.

12. The system as recited in claim 11 where said attachment flange having an adhesive coating for releasably coupling said attachment flange to said annular flange of said condom.

13. The system as recited in claim 11 where said prophylactic means includes Velcro attachment means, said Velcro attachment means being adhesively coupled to said annular flange of said condom.

14. The system as recited in claim 13 where said hole formed through said protective cover is bounded by an attachment flange adapted for releasable coupling with said Velcro attachment means.

15. The system as recited in claim 1 where said increased wall thickness extends radially about said tubular member, said increased wall thickness defining a non-uniform wall thickness increasing from said open proximal end to said closed distal end for increasing the rigidity thereof.

16. The system as recited in claim 3 where said one-piece formation is formed of a latex material composition.

17. The system as recited in claim 7 where said absorbent material layer is located on the surface of said shield means external to said open end of said tubular member.

* * * * *